United States Patent [19]

Ishikawa et al.

[11] 4,149,533
[45] Apr. 17, 1979

[54] DEVICE FOR IONTOPHORETIC APPLICATION OF FLUORIDE ON TOOTH

[75] Inventors: Tatsuya Ishikawa, Kodaira; Sumio Kuriyama, Tokyo; Yoshinori Takaesu, Morioka; Haruhisa Furuishi, Suita; Yoshio Okuzaki, Hirakata; Seiichi Motomura, Kawasaki; Yoshinori Musha, Chofu, all of Japan

[73] Assignees: Matsushita Electric Industrial Co., Ltd., Osaka; The Lion Dentifrice Co., Ltd., Tokyo, both of Japan

[21] Appl. No.: 841,921

[22] Filed: Oct. 13, 1977

[30] Foreign Application Priority Data

Oct. 13, 1976 [JP] Japan .................................. 51-121949

[51] Int. Cl.² .............................................. A61N 1/32
[52] U.S. Cl. .................... 128/172.1; 128/409
[58] Field of Search ............. 128/172.1, 405, 407–409, 128/419 R, 421–423

[56] References Cited

U.S. PATENT DOCUMENTS

| | | | |
|---|---|---|---|
| 3,019,787 | 2/1962 | Simmons | 128/172.1 |
| 3,163,166 | 12/1964 | Brant et al. | 128/172.1 X |
| 3,215,139 | 11/1965 | Dietz | 128/172.1 |
| 3,234,942 | 2/1966 | Simor | 128/172.1 |
| 3,518,996 | 7/1970 | Cortina | 128/422 |
| 3,645,260 | 2/1972 | Cinotti | 128/172.1 |
| 3,908,669 | 9/1975 | Man et al. | 128/422 |
| 3,989,051 | 11/1976 | Nozhnikov et al. | 128/421 |

FOREIGN PATENT DOCUMENTS 1097200 12/1967 United Kingdom ................. 128/172.1

Primary Examiner—Lee S. Cohen
Attorney, Agent, or Firm—Burgess, Ryan and Wayne

[57] ABSTRACT

In order to electrically apply fluoride by means of iontophoresis on a tooth an intermittent direct current is made to flow through the tooth. More particularly, the intermittent direct current has a waveform whose leading edge immediately rises to a peak and which decreases exponentially in time. As a result electrochemical polarization may be avoided and the ratio of the current conduction time to the repetition period may be increased so that the uptake efficiency of fluoride by the tooth may be considerably improved in a smooth manner without the need of impressing an excessive current on the tooth. Therefore adverse effects on nerve systems may be avoided, a patient under treatment feels no pain and no unpleasant stimulus, and the tooth's substance may be so improved as to be free from dental caries or decay.

9 Claims, 13 Drawing Figures

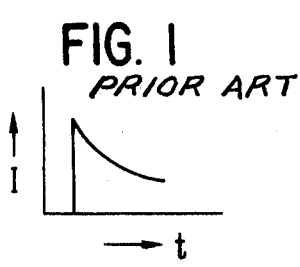
FIG. 1 PRIOR ART
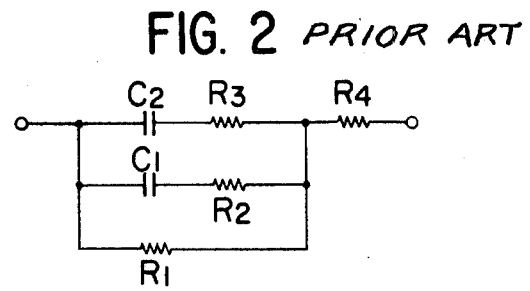
FIG. 2 PRIOR ART
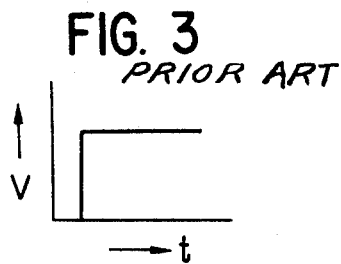
FIG. 3 PRIOR ART
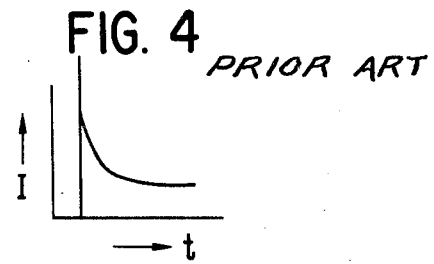
FIG. 4 PRIOR ART
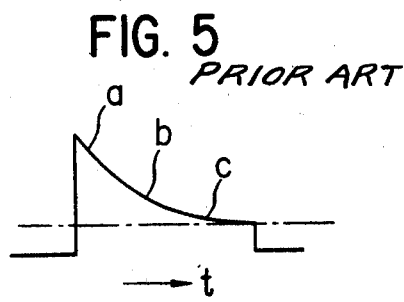
FIG. 5 PRIOR ART
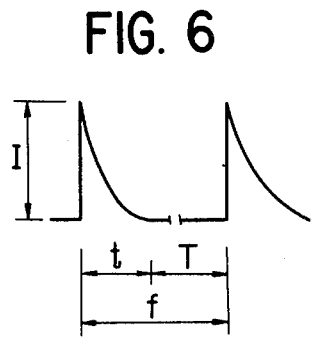
FIG. 6
FIG. 7
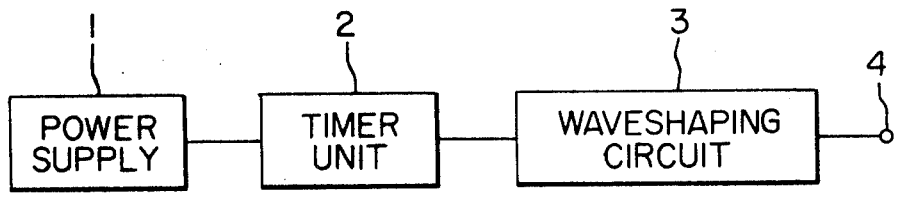

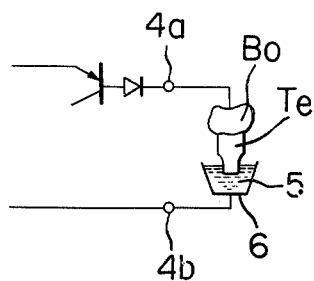
FIG. 8
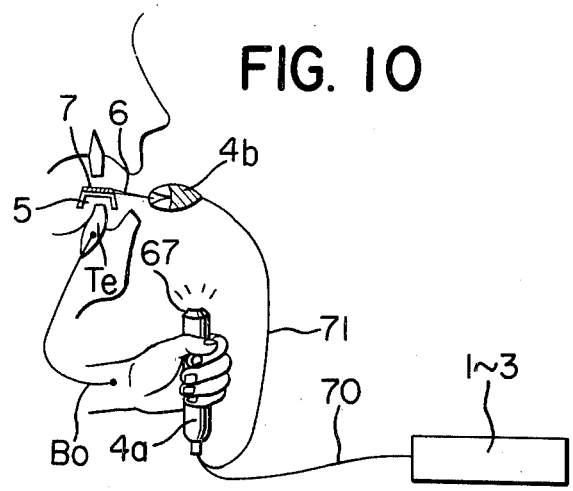
FIG. 10
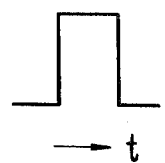
FIG. 11
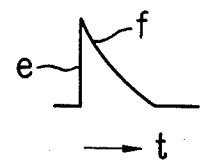
FIG. 12
FIG. 13
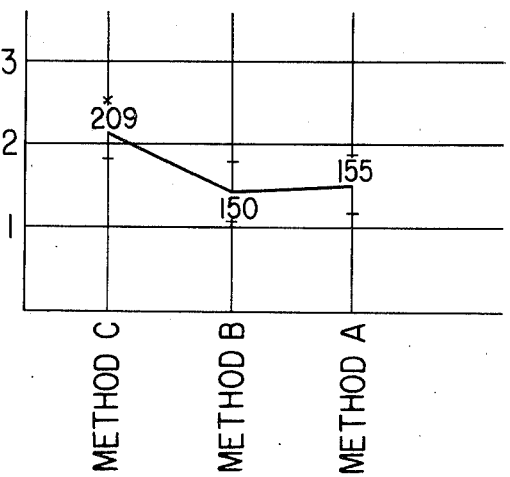

DEVICE FOR IONTOPHORETIC APPLICATION OF FLUORIDE ON TOOTH

BACKGROUND OF THE INVENTION

The present invention relates to generally a device for fluoride iontophoresis on the teeth of not only human beings but also other various forms of life for avoiding dental caries and more particularly a device for fluoride iontophoresis on the teeth of a baby, infant or children for avoiding dental caries of deciduous and young permanent teeth.

In general, the more quantity of sugar one takes, the more one is easily susceptible to dental caries. The incidence of dental caries is relatively high among children. Brushing teeth is the oldest and simplest method for avoiding dental caries, but it is difficult to form the habit of brushing teeth in children having the highest incidence of dental decay. Therefore the national statistics still shows a high percentage of incidence of dental caries. One of the various methods so far investigated for reducing the high incidence of dental caries in children and in young adolescents is to improve the tooth's substance and especially the surface layer of the tooth. That is, the body of the tooth consists of dentin which is mainly composed of calcium phosphate and which is covered by enamel in the crown. The enamel consists of prisms and interprismatic substances and is mainly composed of calcium phosphate (hydroxy apatite). The enamel is by far harder and physically and chemically more stable than the dentin. The susceptibility to dental decay is dependent upon one's age, physical constitution and living conditions (including diet). In general, it is considered that dental caries are started by the decalification of the enamel by bacteria produced acids. Dental caries has been defined as a gradual, progressive destruction of the hard portions of the teeth starting from decalification. The hard portions of the teeth may be made resistant to calicification by growing dense crystals of calcium phosphate or by converting the hard portions into crystals of fluoro apatire.

To this end, the introduction or injection of fluoride into the enamel of the teeth is very effective for preventing dental caries. In practice, aqueous solutions and gels of sodium fluoride and stannous fluoride have been used. That is, these solutions or gels are subjected to hydrolysis so that fluorine may be absorbed into the teeth in the form of ions. The uptake of fluoride ions not only help grow the dense crystals of calcium phosphate but also improves the tooth's substance so that the enamel may not be liable to dental caries. Thus dental decay prevention may be attained.

In order to add fluoride into the teeth, a small amount of fluoride may be added to communal drinking water; a patient may hold in his mouth an aqueous solution of sodium fluride or stannous fluoride; an aqueous solution of sodium fluoride having a relatively high concentration of 1-3% may be applied to the teeth; and fluoride ions may be electrically absorbed into the teeth. Of these methods, the electrical absorption method is most favorable.

The prior art method for iontophoretic application of fluoride ion into the teeth is such that an aqueous solution of sodium fluoride or stannous fluoride is subjected to electrolysis to produce negative fluoride ions which are absorbed into a tooth which is maintained at a positive potential as an anode. In general, the human body is mainly composed of various water soluble electrolytes so that it is considered that the passage of current through the body is the movement of ions or the ion conduction. The use of direct current for the movement through a substance of ions causes the physical and chemical changes of the substance and the electrochemical polarization so that when the current is used, polarization occurs. The polarization is such that the substances produced on the electrodes by hydrolysis cause a chemical reaction which is just the reverse of the hydrolytic reaction. Furthermore the use of smooth direct current results in variation in concentration of electrolyte so that a counterelectromotive force may be produced. Thus as a result of the polarization or counterelectromotive force, the direct current rises its peak at the instant when it starts to flow, and then decreases exponentially in time. The equivalent circuit of the tooth constructed based upon the observation of the behavior of the direct current in the tooth has a time constant or CR parameter. When a direct current is made to flow through this circuit, it immediately reaches its peak, then abruptly decreases and gradually approaches a flat and stable current. Same is true for the passage of direct current through the human body. That is, the direct current flowing through the body decays exponentially so that it takes an impracticably long time before a desired quantity of fluoride ions is absorbed into the tooth.

According to the experiments conducted by the inventors, the magnitude of the initial current or peak is a few times as high as the stable current. Therefore when a direct current is made to flow through the human body, the polarization which results in such a high ratio of the peak current to the stable current must be taken into consideration. In other words, the effects of the passage of direct current through the human body on the various nerve systems must be taken into consideration. Thus for the electrical uptake of fluoride ions by the teeth a method for flowing a direct current through the human body must be employed which will not only avoid of the injuries to the human body but also result in the efficient uptake of fluoride ions by the teeth.

In order to avoid the polarization, in general an alternating current has been used which reaches maximum in one direction, decreases to zero, then reverses itself and reaches maximum in the opposite direction. However when the aqueous solution of sodium fluoride is subjected to hydrolysis or dialysis, sodium fluoride is dissociated into positive sodium ions $Na^+$ and negative fluoride ions $F^-$. The negative fluoride ions $F^-$ are absorbed into a tooth which is maintained at a positive potential as an anode. The use of the alternating current may eliminate the polarization because the alternate change in polarity of electrodes, but the alternating current also causes the alternate change in direction of movement of fluoride ions so that the fluoride ions cannot be accumulated in the tooth. Thus the use of the alternating current in a method for electrical uptake of fluoride ions by the teeth is inpracticable.

SUMMARY OF THE INVENTION

The present invention was made to solve the above and other problems encountered in the prior art methods for electrical uptake of fluoride ions by the teeth. One of the objects of the present invention is therefore to provide a device for fluoride iontophoresis on a tooth which employs an intermittent direct current having a waveform to be described in detail hereinafter so that the polarization may be eliminated and the polarities of electrodes may remain unchanged so as to effect the effective fluoride ion accumulation in the treated tooth.

To this end, briefly stated the present invention provides a device for uptake of fluoride ions by the teeth comprising means including an electrolyte containing fluoride and an electrode brought into electrical contact with the electrolyte which in turn is brought into electrical contact with a tooth to be treated; a positive terminal brought into electrical contact with the body of a patient; a negative terminal brought into electrical contact with the electrode brought into contact with the electrolyte; and means for flowing an intermittent direct current through the body of the patient from said positive terminal to said negative terminal.

BRIEF DESCRIPTION OF THE DRAWINGS

FIG. 1 is a graph illustrating a waveform of a direct current flow through an ion conduction mechanism;

FIG. 2 is an equivalent circuit diagram of a tooth;

FIG. 3 shows a waveform of an ideal direct current;

FIG. 4 shows a waveform of the ideal direct current when made to pass through the equivalent circuit shown in FIG. 2;

FIG. 5 is a view used for the explanation of the waveform shown in FIG. 4;

FIG. 6 shows a waveform of an intermittent direct current which is employed in the present invention and which decreases exponentially in time;

FIG. 7 is a block diagram of one preferred embodiment of a device for iontophoretic application of fluoride on the teeth in accordance with the present invention;

FIG. 8 shows an electrical arrangement of a tooth to be treated, an electrolyte and an electrode between positive and negative terminals of the device shown in FIG. 7;

FIG. 10 shows how the positive and negative terminals of the device are set relatively to the body of a patient;

FIG. 11 shows a rectangular wave generated in a waveshaping circuit of the device;

FIG. 12 shows an exponentially decreasing wave converted from the rectangular wave shown in FIG. 11 in the waveshaping circuit; and FIG. 13 is a graph illustrating the comparison of the effects of the present invention and two prior art methods, the effect being shown in terms of a ratio of a quantity of fluoride ion in a tooth after treatment to a quantity of fluoride ion in the same tooth before treatment.

DESCRIPTION OF THE PREFERRED EMBODIMENT

Prior Art, FIGS. 1-5

Figure 9:
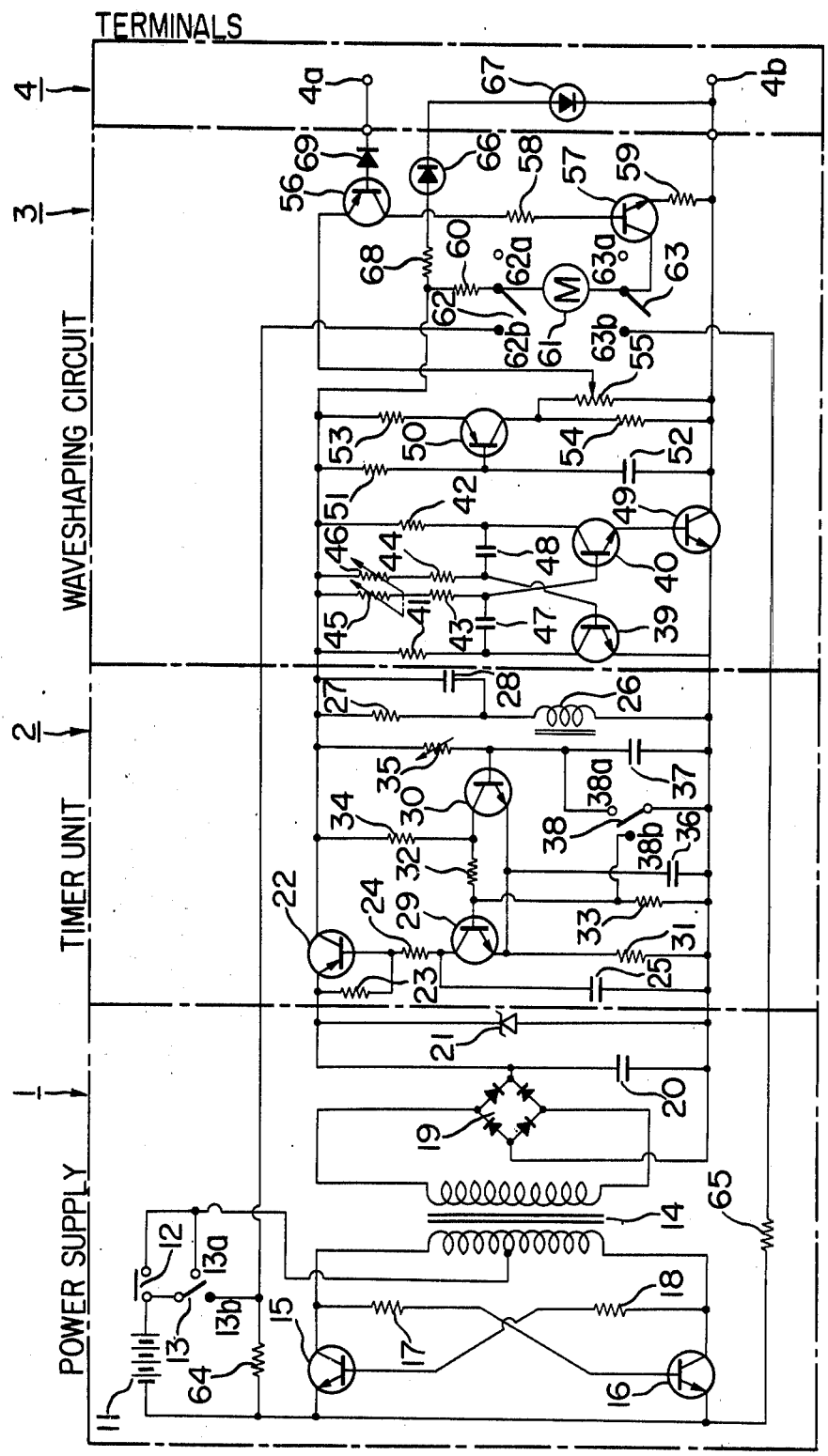
FIG. 9 is a detailed circuit diagram of the device shown in block diagram in FIG. 7.

Prior to the description of a preferred embodiment of the present invention, prior art fluoride iontophoresis methods will be described with reference to FIGS. 1-5. One of them is electrically injecting fluoride into a tooth. That is, a tooth is used as an anode, and an aqueous solution of sodium fluoride or stannous fluoride is ionized to produce nagative ions or fluoride ions which are absorbed into the anode or tooth. Since a human body mainly consists of various water soluble electrolytes, the passage of current through the body is considered to be associated with the ion conduction. When a direct current is used in an ion conduction mechanism where the passage of current is associated with the movement of ions, substances are subjected to changes and the polarization occurs so that the correct current conduction cannot be attained. That is, when a smoothed direct current is used in the ion conduction mechanism, the polarization that a substance produced on the surface of an electrode due to the passage of current causes chemical reactions and a reversal chemical reaction caused by the passage of current occurs. That is, a counterelectromotive force is produced due to the variation in concentration of an electrolyte. As a result the current reaches a peak or maximum value immediately after the current has been started to flow and decreases in magnitude as the time elapses. This phenomenon is shown in FIG. 1. Based upon the behavior of this direct current, an electrically equivalent circuit of a tooth is obtained as shown in FIG. 2. Obviously the operation of this circuit is dependent upon a CR parameter. When a direct current as shown in FIG. 3 is made to flow through this circuit, [an output] current immediately rises to a peak and then abruptly decrease and then gradually reaches a stable current as shown in FIG. 4. Therefore when the direct current as shown in FIG. 3 is made to flow through a human body, the current decrease is exponentially dependent upon a CR time constant so that the uptake of fluoride ions by a tooth of [a desired amount of] fluoride ions takes impracticably a long time.

Furthermore, the experiments showed that the initial current is a few time greater than the stabilized current. Thus, when a current is made to pass through a human body, a large current ratio due to the polarization must be taken into consideration. That is, the human body has the motor, sensor and autonomic nerve systems, and the effects on them by the passage of current must be taken into consideration. Dangerous phenomena such as damages to organic structures due to the negligence of these effects must be completely avoided at any cost, and a method for passing a current through the human body in order to efficiently effect an uptake of the fluoride ions into an object tooth must be devised.

In the current conduction due to the ion conduction mechanism, an alternating current is in general employed in order to avoid the polarization. The polarities of the alternating current change as a function of time. The results of one experiment will be described. When the hydrolysis or dialysis of an aqueous solution of sodium fluoride is employed so as to absorb the fluoride ions into a tooth, sodium fluoride is dissociated into $Na^+$ and $F^-$; that is,

$$NaF \rightarrow Na^+ + F^-$$

When the tooth is electrically raised to a positive potential, the fluoride ions $F^-$ are absorbed into the enamel of the tooth. When an alternating current is employed in fluoride iontophoresis, the effects of the polarization which is an electrochemical phenomenon caused in the human body may be avoided from accumulating because these effects are cancelled by the alternating changes of the current polarities. However, since the direction of current changes, it becomes impossible to absorb and accumulate the ions in the tooth. As described above, the effects of the polarization due to the use of a direct current may be avoided by the use of an alternating current, but when the alternating current is used, it is impossible to accumulate the ions.

Next, the underlying principle of the present invention will be described. An intermittent direct current which is generally used has a rectangular waveform having a considerably steep leading edge so that it gives a strong stimulus to the human body and consequently it cannot be used in practice. When an intermittent direct current (having a rectangular waveform) is made to pass through a tooth, the [output] current as shown in FIG. 4 is obtained. From the equivalent circuit, the behavior of the current passing through the tooth may be approximately expressed by the CR parameter described above. In order to observe the behavior of the [output] current when a square wave is impressed on a CR time constant circuit, the relationship between the CR time constant and the frequency of the square wave was studied. The results are (A) that when the CR time constant is shorter than one half cycle of the square wave, the flow of current is very small and the current having a differentiated waveform flows, (B) that when the CR time constant is equal to one half cycle of the square wave, the current values at the initial stage and intermittent stage have different values so that the output which is substantially similar in waveform to the input cannot be attained, and (C) that when the time constant is longer than the half cycle of the square waveform, a square wave which is more correct in shape than the output obtained in (B) may be obtained. That is, the greater the time constant than one half cycle of the square wave, the more correct the waveform of the output becomes. The relationship between the time constant and the period may be defined by the waveform similarity P which gives the degree of similarity in waveform between an input and an output. That is, $$P = 100 T/2CR (\%)$$

where
T = a period, and
CR = a time constant.

The waveform similarity P shows that the smaller the value of P is, the more similar in waveform to the input the output becomes. In terms of frequencies the waveform similarity P is also given by $$P = 100 \cdot \pi \cdot (f_1/f)(\%)$$

where $\pi$ = the circular constant, 3.14,
f = the repetive frequency of a square wave, and
$f_1$ = a frequency with which the reactance of a capacitor becomes equal to the resistance of a resistor.

It is seen that to obtain P less than 10%, T/2 must be less than 1/10 of the time constant CR or f must be higher than 31.4 times $f_1$. The complete charging or discharging of a capacitor requires a time longer than 10 time constants. Thus it follows that in order that 10 CRs which is required for charging the capacitor may be satisfactorily short, the charging time must be less than 1/10 of the time constant CR. Otherwise the residual potential or voltage accumulates on the capacitor so that the current conduction is intermittent. However, it takes a considerably long time constant to cause the capacitor to be completely discharged. As a consequence, a current conduction time becomes shorter in practice, and the quantity of electricity decreases so that it takes an extremely long time before a desired quantity of ions can be absorbed into a tooth.

Therefore in order to pass a desired quantity of electricity without causing the decrease in overall quantity of electricity, a pulse with a less direct current component must be passed within a time interval shorter than a time constant so that the discharge time may be increased. The inventors found the waveform most suitable for this purpose. First, a waveform shown in FIG. 5 is analyzed in order to investigate the current conduction characteristics obtained from an equivalent circuit. The waveform shown may be expressed in terms of three CR constants a, b and c. They are 10 msec, 80–100 msec and 1000 msec, respectively. The flat portion c has a large time constant so that it takes an extremely long time (about 10 times) before the charges on the capacitor may be discharged. Furthermore, this waveform has a large direct current component so that the polarization results as described above and consequently the current conduction effect is decreased. Therefore the most effective current conduction method is to cut off the portion c, to concentrate a peak around the portions a and b and to remove the direct current component as much as possible. Such a waveform is shown in FIG. 6. That is, the current immediately reaches its peak and immediately decays exponentially, and no direct current component is included. With this intermittent direct current which, when made to pass through the human body, immediately reaches its peak and exponentially decays in time, even when the ratio of the current conduction time to the repetitive period of this intermittent direct current is increased to as high as ½, the complete charging and discharging may be effected without the accumulation of the residual potential and the polarization may be completely eliminated. However when the above ratio is decreased as low as 1/10, it will take a long time to absorb a desired quantity of fluoride ions as described above. Therefore when the intermittent direct current having the waveform described above is employed, the above ratio is preferably between 1/10 and ½.

In order to carry out the present invention, the intermittent direct current having a waveform wherein the leading edge immediately reaches the peak and immediately starts to decrease exponentially must be used, and the ratio of the current conduction time to the repetitive period of the intermittent direct current must be between ½ and 1/10. Three factors; that is, the frequency of the intermittent direct current, the voltage and the current conduction time are selected depending on the [physical] characteristics (quality of tooth) of a patient as described below. The decomposition voltage of the aqueous solution of sodium fluoride is $$5.563 V (Na^+ = 2.713 V, F^- = 2.85 V)$$

and the decomposition voltage of an aqueous solution of stannous fluoride is $$2.99 V (Sn^+ = 0.14 V, F^- = 2.85 V)$$

Therefore the voltage must exceed these decomposition voltages. The frequency is preferably between 5 Hz and 1 KHz and more preferably between 100 Hz and 200 Hz. The voltage E is preferably between 3 and 15 V and more preferably between 6 and 9 V. The current I is preferably between 50 and 500 A and more preferably between 100 and 150 $\mu$A. When the frequency is lower than 5 Hz, the current conduction effect is decreased while the current conduction time increases. Thus, the frequency less than 5 Hz is not preferable in practice. On the other hand when the frequency exceeds 1 KHz, the recovery from the polarization cannot be attained so that the advantages offered by the use of the intermittent direct current are lost. When the current I is less than 50 µA, less ion injection results so that the satisfactory effect cannot be obtained. On the other hand when the current I exceeds 500 µA, a stimulus to the human body becomes too strong so that the current exceeding 500 µA cannot be used in practice. In order that the current I may be within 50 and 500 µA, the voltage must be between 3 and 15 V.

In FIG. 7 there is shown a block diagram of the device in accordance with the present invention comprising a power supply 1, a timer unit 2 and a waveshaping stage or circuit 3 the output of which is derived from terminals 4. As shown in FIG. 8, a positive terminal 4a is brought into contact with the body of a patient so that the tooth Te may serve as an anode while a negative terminal 4b is connected to an electrode 6 which in turn is connected to an electrolyte 5 containing fluoride and being brought into contact with the teeth Te, whereby an ion injection circuit is established. The power supply 1 may be an AC or DC power supply. When an AC power supply is employed, the power supply voltage must be stepped down to a predetermined level and special measures must be taken into consideration so that the patient may be protected against electrical damages due to leakage current. With a DC power supply, a low voltage must be stepped up to a desired level by an inverter or the like, but this is not necessary when a predetermined voltage may be obtainable. When an inverter is employed, the output must be rectified so as to provide a stable DC power supply. In general, it is preferable to step up a low DC power supply and rectify so as to provide a DC power supply. A timer unit 2 comprises a variable timer consisting of semiconductor circuits and starts counting a time as soon as the power supply is turned on for iontophoresis and disables the power supply after a predetermined time. Thus the time unit 2 serves to control the quantity of fluoride ions to be absorb and to rationalize the iontophoresis operation. Next the waveshaping circuit 3 comprises a circuit for converting a time-controlled direct current into a rectangular wave and a circuit for converting the rectangular wave into an exponentially decreasing waveform. The above three stages constitute the major part of the present invention. The waveshaping circuit 3 may include an ammeter and a current-conduction display lamp. Preferably the positive terminal 4a is made of an electrically conductive metal and is of such a size that even a baby may hold it by one hand and includes a cord and a light-emitting display means. The negative terminal 4b is preferably in the form of a clip so that it may be readily connected to the electrode which in turn is brought into contact with the electrolyte containing fluoride. In addition, it is preferable that a time interval set by the timer unit and an frequency and current magnitude of the output from the waveshaping circuit are also variable within the limits described above.

Now one preferred embodiment of the present invention will be described in conjunction with the accompanying drawings.

In FIG. 9 there is shown a circuit diagram thereof. In general it comprises the power supply 1, the timer unit 2, the waveshaping circuit 3 and the terminals 4. In the power supply 1, 11 is series-connected batteries; 12, a relay switch; 13, a manually operable, single pole, double throw, center off switch. This switch 13 consists of a knob which is movable in two opposite directions; that is, to the right and left or back and forth and remains at the center when no force is exerted thereto. When one pushes this knob in one direction, one a of normally opened contacts is closed, and when one pushes the knob in the other direction, the other normally open contact b is closed. When one releases the knob, the latter returns to the center position so that both the normally open contacts a and b are opened. 14 is a step-up transformer; 15 and 16, transistors; 17 and 18, resistors. They constitute a self-excited oscillator. 19 is a rectifier consisting of a diode bridge for full-wave rectifying the secondary voltage of the step-up transformer 14; 20, a smoothing capacitor; 21, a zener diode. They serve to convert the secondary voltage of the step-up transformer 14 into a stabilized direct current or voltage. In the timer unit 2, 22 is a transistor which effects the switching operations; 23 and 24, resistors; 25, a capacitor; 26, a relay coil for controlling the switching operations of the relay switch 12; 27, a resistor; and 28 a capacitor. Therefore when a normally open contact 13a of the manual switch 13 is closed, the relay coil 26 causes the relay switch 12 to turn on so that even when the manual switch 13 is turned off, the relay switch 12 is kept turned on. That is, they constitute a self-holding or self-latching circuit. 29 and 30 are transistors; 31–34, resistors; 35, a variable resistor for a timer for adjusting a time interval; 36, a capacitor; and 37, an electrolyte capacitor having a large capacity. They constitute a timer circuit. A predetermined time after the transistor 22 is turned on, it is turned off so that the supply of current to the relay coil 26 is intermittent and consequently the relay switch 12 is also turned off. This time is called a timer time which may be adjusted by the variable resistor 35. 38 is a single pole, double throw, center off, manual switch. In the waveshaping circuit 3, 39 and 40 are transistors; 41–44, resistors; 45 and 46, variable resistors for adjusting the frequency of oscillation; 47 and 48, capacitors. They constitute a self-excited oscillator which generates a rectangular wave output as shown in FIG. 11, and the output is amplified by a transistor 49. The frequency is adjustable by the variable resistors 45 and 46. 50 is a transistor; 51, a resistor; 52, a capacitor; 53 and 54, resistors and 55, a variable resistor. They constitute a waveshaping circuit which generates a waveform which exponentially decays. That is, this circuit causes the rectangular wave (See FIG. 11) to exponentially decay as shown in FIG. 12. 56 and 57 are transistors; 58–60, resistors and 61, a load current indicator. They constitute a current indicator circuit for indicating the magnitude of current flowing to the terminal 4a. 62 and 63 are manually operable, single pole, double throw, center off switches. The four single pole, double throw, center off switches 13, 38, 62 and 63 described above are ganged in such a way that one may push one knob so as to close either of the normally open contacts a or b. 64 is a resistor which serves as a dummy load, and 65, a resistor. When the normally open contacts b of the manual gang switches 13, 38, 62 and 63 are closed, the dummy load 64 is connected to the batteries 11 and the voltage level of the latter is indicated by the meter 61 and the timer unit 2 is reset. 68 and 67, light emitting display consisting of light emitting diodes (LDE); and 66, a resistor. The light-emitting display devices 66 and 67 are turned on and off in synchronism with the transistor 49, and constitute the current-conduction display circuit which indicates the flow of current to the terminals 4. Furthermore they also serve as a discharge circuit of the capacitor 52. 69 is a diode connected in series to an output terminal extended from the base of the transistor 56 of the waveshaping circuit 3. Of the terminals 4, 4a is the positive terminal and 4b, the negative terminal as described above. The magnitude of the current flowing to the terminals 4 may be adjusted by the variable resistor 55.

In FIG. 10 there is shown the setting of the terminals of the device in accordance with the present invention to the human body. The positive and negative terminals 4a and 4b are extended from the output terminals of the main body 1–3 of the iontophoresis device through cords 70 and 71. The positive terminal 4a consists of a cylinder made of an electrically conductive metal and in such a size that a baby or infant may hold it. The light emitting display device 67 is attached to the top of the cylindrical positive terminal 4a. That is, since the patients or those through whom the current flows are almost babies and infants, they hardly maintain stable posture required for treatment even when the current conduction time is only a few minutes. The light emitting display device 67 at the top of the terminal 4a is therefore turned on and off so as to please the baby or infant under treatment. The negative terminal 4b is in the form of a clip so that the connection to or disconnection from the electrode 6 may be facilitated. NaF aqueous solution 5 is immersed in a sponge which in turn is contained in a tray 7 provided with the electrode 6 at the bottom. The solution 5 is brought into contact with the tooth Te of the body Bo. Under the conditions shown in FIG. 10, the tooth and the arm are at the same positive potential.

In use of the device with the above construction, first the device is set as shown in FIG. 10, and one operates the knob of the manual gang switches 13, 38, 62 and 63 so as to turn on the normally open contacts instantly. Then the self-excited oscillator mainly consisting of the transistors 15 and 16 starts oscillation, and the output is stepped by the step-up transformer 14. The secondary voltage of the transformer 14 is rectified, smoothed and stabilized by the rectifier 19, the capacitor 20 and zener diode 21 so that the stabilized direct current voltage may be obtained. The charging current flows through the resistors 23 and 24 into the capacitor, and the transistor 22 is turned on. When the transistor 22 is turned on, the current flows through the resistor 27 into the relay coil 26 to energize the latter so that the relay switch 12 is turned on. Meanwhile the voltage across the timer capacitor 37 is low so that the transistor 30 is turned on while the transistor 29 is turned on. As a result the transistor 22 is kept turned on so that even when the manual switch 13 is turned off, the above described operation is kept and the relay switch 12 remains turned on. As soon as the relay switch 12 has been turned on the oscillation of the self-excited oscillator mainly consisting of the transistors 39 and 40 is started so that the square wave as shown in FIG. 11 is generated. This wave is amplified by the transistor 49. The square wave causes the current to flow through the resistor 53, the emitter and base of the transistor 50 and the capacitor 52 so that the capacitor 52 is charged. This charging current is current-amplified by the transistor 50. The voltage which exponentially decreases as shown in FIG. 12 appears across the variable resistor 55. This waveform is such that as soon as the current conduction is started, the current rises to the maximum (indicated by e) and exponentially decreases in time (as indicated by f). This waveform is transmitted through the terminals of the variable resistor 55, the emitter and base of the transistor 56 and the diode 69 to the terminal 4. This waveforms flows from the positive terminal 4a through the body Bo, the tooth Te, aqueous solution 5 of sodium fluoride and the electrode 6 to the negative terminal 4b. As a result, the sodium fluoride is dissociated into Na ions and F ions. The fluoride ions (negative ions) are absorbed into the tooth Te which is the anode.

Meanwhile the collector current of the transistor 56 flows through the resistor 58, the base and emitter of the transistor 57 and the resistor 59. As a result the collector current of the transistor 57 which is in proportion to the base current thereof flows through the resistor 60 and the meter 61 into the transistor 57. That is, the base current of the transistor 56 flowing to the positive terminal 4a is amplified by the transistors 56 and 57 and is indicated on the meter 61. One adjusts the variable resistor 55 depending upon the indication on the meter 61 so as to adjust the current flowing from the positive terminal 4a to the negative terminal 4b. Since this circuit is a current feedback circuit, even when the frequency of the rectangular wave becomes longer or higher, the meter always correctly operates. Furthermore the light emitting display devices 66 and 67 are turned on and off in synchronism with the transistor 49; one may see that the iontophoresis device is in the ON state. Since the light emitting diode 67 is attached to the positive terminal 4a as described above, it serves as a very effective display device for pleasing the baby or infant during treatment.

When the intermittent direct current flows in the manner described above, the timer capacitor in the timer unit 2 is charged with the current flowing through the variable resistor 35. After a suitable charging time (which is in general a few minutes) the voltage across the capacitor 37 rises to a level with which the transistor 30 is turned on. This time is referred to as "a timer time" which may be increased when the variable resistor 35 is made greater (has a high value) or which may be shortened when the variable resistor 35 is made smaller (has a low value). When the transistor 30 is turned on the transistor 39 is turned off and the transistor 22 is also turned off. As a result, the supply of current to the relay coil 26 is interrupted so that the relay switch 12 is turned off and consequently the operation of the whole iontophoresis device is interrupted. That is, no current flows from the positive terminal 4a to the negative terminal 4b and consequently the injection of fluoride ions into the tooth Te is stopped.

When one pushes the knob of the manual gang switches 13, 38, 62 and 63 so as to close the normally open contacts b, the dummy load 64 is connected to the batteries 11, and the series-connected circuit consisting of the manual switch 62, the meter 61, the manual switch 63 and the resistor 65 is connected in parallel with it so that the meter 61 indicates the voltage level of the batteries 11. When one desires to interrupt the current conduction before the normal current conduction is completed, one may turn on the normally open contacts b of the manual gang switches, 13, 38, 62 and 63. Then the manual switch 38 grounds the base of the transistor 29 thereby turning it off so that the transistor 22 is also turned off. As a result, the relay switch 12 is turned off in the manner described above so that the current conduction is interrupted. In order to compare the effect of the intermittent current (C) on the fluoride uptake in the enamel with that of the direct current (B) and conventional topical application (A) procedures, the inventors made an experiment in VIVO. The current of both methods (B and C) was set at 150 $\mu$A. In each pair of central and lateral incisors, one side was treated with and the other was not treated with 2% NaF gel. Enamel biopsies were done on these samples to determine fluoride uptake. However, the biopsies were done imediately after treatment and a week later for each pair. The comparisons of the uptake of fluoride were made using the ratio of the fluoride contents of the treated and untreated tooth in each pair. The a part of data was shown in Table below.

| Measuring time | After introduction | | | After one week | | |
|---|---|---|---|---|---|---|
| method | A | B | C | A | B | C |
| group 1 | 2.05 | 2.05 | 3.07 | 1.14 | 1.00 | 1.42 |
| group 2 | 1.15 | 2.63 | 3.61 | 0.98 | 1.74 | 1.88 |

It is seen that the quantities of ions absorbed with the iontophoresis device in accordance with the present invention are by far greater than the quantities absorbed by the methods A and B. Furthermore the quantities of fluoride ions in the teeth one week after treatment are also by far greater than the quantities by the methods A and B.

Further experiments were made in order to compare the above three methods A, B and C, and the results are shown in FIG. 13. In FIG. 13 the mean values and the 95% confidence intervals are shown. These data show the statistic superiority of the present invention over the prior direct application and method B. Furthermore the experiments showed that the present invention is superior to the prior art methods by higher than 40% in terms of the fluoride absorption increasing rate.

What is claimed is:

1. A device for injecting fluoride ions into a tooth comprising
    means including an electrolyte containing fluoride and an electrode in electrical contact with said electrolyte, said electrolyte being adapted for contact with a body;
    a positive terminal adapted for electrical contact with said body;
    a negative terminal in electrical contact with said electrode; and
    a current conduction means for permitting an intermittent direct current to flow between said positive and negative terminals, said current conduction means generating an intermittent direct current having a waveform which reaches a maximum level immediately after the current conduction is started and thereafter decays in time.

2. A device as set forth in claim 1 wherein said waveform of said intermittent direct current decreases exponentially in time.

3. A device as set forth in claim 2 wherein the ratio of the conduction time to the repetitive period of said intermittent direct current is between 1/10 and ½.

4. A device as set forth in claim 3 wherein said intermittent direct current has a frequency between 5 Hz and 1 KHz and a magnitude between 50 $\mu$A and 500 $\mu$A.

5. A device as set forth in claim 1 wherein the ratio of the conduction time to the repetitive period of said intermittent direct current is between 1/10 and ½.

6. A device as set forth in claim 5 wherein said intermittent direct current has a frequency between 5 Hz and 1 KHz and a magnitude between 50 $\mu$A and 500 $\mu$A.

7. A device as set forth in claim 1, wherein said current conduction means comprises:
    power supply circuit means for generating a stabilized direct current output, said power supply circuit means including switching means interconnected between a power supply and a load.
    timer circuit means for turning off said switching means a predetermined time after said power supply circuit means has started to generate said directed current output, and
    waveshaping circuit means actuable in response to said direct current output from said power supply circuit means for oscillating and thereby generating an intermittent direct current, said waveshaping circuit means comprising
        (a) a self-excited oscillator which is actuated in response to the direct current output from said power supply circuit means to oscillate, thereby generating a rectangular wave, and
        (b) a waveform converting circuit means for converting said rectangular wave into a waveform which reaches a maximum level immediately after the current conduction has been started and decreases exponentially in time.

8. A device as set forth in claim 7 wherein said timer circuit means includes a timer variable means for adjusting a timer time; and said waveshaping circuit means includes an intermittent time variable means for adjusting an intermittent time of said intermittent direct current, and a load current variable means for adjusting the magnitude of said intermittent direct current flowing between said positive and negative terminals.

9. A device as set forth in claim 7 wherein said waveshaping circuit means includes light emitting display means which is turned on and off by said intermittent direct current, said light emitting display means being mounted on said positive terminal.

* * * * *

UNITED STATES PATENT OFFICE
CERTIFICATE OF CORRECTION

Page 1 of 2

Patent No. 4,149,533  Dated April 17, 1979

Inventor(s) Tatsuya Ishikawa, et al

It is certified that error appears in the above-identified patent and that said Letters Patent are hereby corrected as shown below:

In the Drawings, Figure 13: "FRUORIDE" (both occurrences) should be --FLUORIDE--; "209" should be --2.09--; "150" should be --1.50--; "155" should be --1.55--.

Column 1, lines 35 and 38: change "decalification" to --decalcification--.

line 39: change "calicification" to --decalcification-- line 41: change "apatire" to --apatite--.

line 56: change "fluride" to --fluoride--.

lines 48, 58, 63 and 65: change "fluoride" to --fluorine--.

Column 2, lines 26, 37, 41, 49 (both occurrences), 55 (both occurrences), 58, 63: change "fluoride" to --fluorine--.

Column 3, lines 2, 4, 50, 51 and 62: change "fluoride" to --fluorine--.

line 63: change "nagative" to --negative--.

Column 4, lines 25, 39, 47 (last occurrence) and 54: change "fluoride" to --fluorine--.

Column 5, line 45: change "repetive" to --repetitive--.

UNITED STATES PATENT OFFICE
CERTIFICATE OF CORRECTION

Patent No. 4,149,533    Dated April 17, 1979

Inventor(s) Tatsuya Ishikawa, et al

It is certified that error appears in the above-identified patent and that said Letters Patent are hereby corrected as shown below:

Column 6, line 31:  change "fluoride" to --fluorine--.

line 61:  change "500A" to --500μA--.

Column 7, line 37:  change "fluoride" to --fluorine--.

line 38:  change "absorb" to --absorbed--.

Column 8, line 26:  "constiture" should be --constitute--.

line 61:  change "LDE" to --LED--; change "66" to --68--.

Column 10, lines 4 and 46:  change "fluoride" to --fluorine--.

Column 11, line 14:  change "1.14" to --1.41--.
line 15:  change "1.88" to --1.83--.
line 36:  change "flouride" to --fluorine--.

Signed and Sealed this

Eighteenth Day of September 1979

[SEAL]

Attest:

LUTRELLE F. PARKER
Attesting Officer    Acting Commissioner of Patents and Trademarks